(12) United States Patent
Mullen et al.

(10) Patent No.: US 7,010,339 B2
(45) Date of Patent: Mar. 7, 2006

(54) HYBRID LIDAR-RADAR FOR MEDICAL DIAGNOSTICS

(75) Inventors: Linda J. Mullen, Chesapeake Beach, MD (US); Vincent M. Contarino, Lusby, MD (US); Peter R. Herczfeld, Philadelphia, PA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 499 days.

(21) Appl. No.: 10/207,642

(22) Filed: Jul. 29, 2002

(65) Prior Publication Data

US 2004/0019282 A1    Jan. 29, 2004

(51) Int. Cl.
*A61B 5/05*    (2006.01)
(52) U.S. Cl. .................. 600/430; 600/407; 600/425; 600/476; 600/478
(58) Field of Classification Search ............... 600/407, 600/430, 478, 9, 476, 473, 182, 425; 435/7.23; 424/9.1, 1.11, 1.49; 606/10, 41; 356/301
See application file for complete search history.

(56) References Cited

U.S. PATENT DOCUMENTS

| | | | |
|---|---|---|---|
| 5,445,608 A * | 8/1995 | Chen et al. ................ 604/20 |
| 5,482,041 A * | 1/1996 | Wilk et al. ................ 600/430 |
| 5,807,257 A * | 9/1998 | Bridges .................... 600/430 |
| 5,829,437 A * | 11/1998 | Bridges .................... 600/430 |
| 5,920,390 A * | 7/1999 | Farahi et al. ............. 356/477 |
| 6,332,087 B1 * | 12/2001 | Svenson et al. ........... 600/407 |
| 6,370,422 B1 * | 4/2002 | Richards-Kortum et al. .................. 600/478 |
| 6,503,478 B1 * | 1/2003 | Chaiken et al. ........... 424/9.1 |
| 6,869,430 B1 * | 3/2005 | Balbierz et al. ........... 606/41 |
| 2003/0088180 A1 * | 5/2003 | Van Veen et al. ......... 600/430 |
| 2003/0187319 A1 * | 10/2003 | Kaneko et al. ............. 600/9 |
| 2004/0009540 A1 * | 1/2004 | Soohoo et al. ........... 435/7.23 |

* cited by examiner

*Primary Examiner*—Eleni Mantis-Mercader
*Assistant Examiner*—Baisakhi Roy
(74) *Attorney, Agent, or Firm*—Mark Glut; Ron Billi

(57) ABSTRACT

A hybrid lidar-radar system for detecting the presence of objects, such as cancerous tumors, within tissues by detecting reflected signals from the tissue and discriminating the information related to the cancerous tumor from the undesirable backscattering of light created by the tissue itself. The hybrid lidar-radar system utilizes continuous wave light that is preferably modulated at frequencies up to 60 GHz. The present invention filters the return signals from the tissue at a subcarrier modulation frequency so as to reject erroneous information contained in scattered lights, while at the same time retaining the coherent, unscattered and modulated light information so as to provide for an accuracy detection of tumors within tissues.

5 Claims, 5 Drawing Sheets

HYBRID LIDAR-RADAR FOR MEDICAL DIAGNOSTICS

STATEMENT OF GOVERNMENT INTEREST

The invention described herein may be manufactured and used by or for the Government of the United States of America for governmental purposes without the payment of any royalties thereon or therefore.

BACKGROUND OF THE INVENTION 1.0. Field of the Invention

The present invention relates to optical imaging of tissues and, more particularly, to a light detection and ranging (LIDAR) system for medical diagnostics particularly suited for detecting the presence of inhomogeneities in tissues, such as tumors.

2.0. Description of the Related Art

The noninvasive and early detection of biological tissue abnormalities with submillimeter dimensions, such as cancerous tumors, is an important challenge and constant improvements are being sought. The well-established X-ray and ultrasound techniques lack the resolution to detect such small objects some of which may be cancerous tumors. In addition, the risk of tissue ionization that may damage healthy tissues prevents the use of X-rays for routine examination. Magnetic resonance imaging (MRI) has submillimeter resolution, but the cost of this technique is still high for general use.

The need for a safe, inexpensive, and efficient method for the early detection of tissue imperfections, such as cancerous tumors, has led to the investigation of optical imaging techniques. For such applications, light between 600 and 1300 nm that falls within a transmission window is minimally absorbed as it propagates through tissue and can therefore be used to non-invasively probe internal structures in search of tissue abnormalities. The existence of this transmission window, combined with the highly forward directed scattering of light, allows for substantial penetration of light in tissue in search of tumors. The main disadvantage of using optical light inside the body is that light is highly scattered by tissue. This optical scattering degrades an image in several different ways. First, some light that does not reach the object, such as the cancerous tumor, is disadvantageously reflected by intervening particles of the tissue itself into the receiver field of view. This backscattered, diffuse light creates a background noise level that degrades the image contrast. Secondly, light that reaches and is reflected from the object encounters small forward angle scattering on its travel back to the receiver and is commonly referred to as snake photons or snake light. These snake photons limit the photon detection and degrade contrast by decreasing the image sharpness or resolution.

Unlike photon limited detection, contrast limited detection cannot be improved simply by increasing the transmitted optical power (or the detector quantum efficiency). However, a method for separating the unscattered or minimally scattered, ballistic or snake photons from the diffuse photons that have been scattered several times could be used to improve object detection and imaging. These improvements may be further described with reference to FIG. 1 composed of FIGS. 1(A), 1(B) and 1(C) illustrating the three most popular approaches for accomplishing this task of improving object detection and imaging and which are a time domain (FIG. 1(A)) approach, a coherence domain (FIG. 1(B)) approach, and a frequency domain (FIG. 1(C)) approach. It is important to note that the approaches depicted in FIG. 1 and FIG. 2, to be described hereinafter, are shown for a transmission type measurement (i.e., the light is transmitted from one side of the tissue and light is detected from the other side of the tissue) to simplify the explanation. These techniques can also be used in a reflection type measurement (i.e., the light is transmitted from one side of the tissue and light is detected from the same side of the tissue).

FIG. 1, as well as FIG. 2, is illustrated in three sections, one section 10 showing the parameters related to transmitting a light signal into the tissue 16 under examination, a second section 12 showing the parameters associated with the signals detected at the other side of the tissue 16, and a third section 14 showing the parameters associated with the signals detected at the other side of the tissue 16 and the measurements performed on these signals. The second section 12 also includes the inhomogeneity 18, such as a cancerous tumor, in the tissue, and a waveform 20 that illustrates a composite scattered signal comprised of the ballistic light 22 that passes straight through the object 18, the snake light 24, and the diffuse light 26.

The time domain approach (FIG. 1(A)) transmits a light pulse 28, in the direction 30, into the tissue 16, and uses differences in the time delay between highly scattered and minimally scattered photons included in the composite reflected signal 20. Light that travels the most direct path, identified as ballistic light 22, between the transmitter and receiver will arrive first, and photons that propagate along longer paths due to multiple scattering identified as snake and diffuse light, 24 and 26, respectively, will arrive at progressively later times. The ballistic light 22 is identified in the received section 14 of FIG. 1(A) as contained in the smaller signal 34, whereas the multiple scattered light 24 and 26 are identified in the received section of FIG. 1(A) as contained in the larger signal 32.

The time domain approach of FIG. 1(A) uses a high speed shutter, generally identified by reference number 36, that is opened for a short time to allow only the early photons associated with the ballistic light 22 to be detected and is then closed to leave out the multiply scattered, delayed photons associated with the multiple scattered light 24 and 26. One associated approach uses a streak camera receiver, which is capable of very short (picosecond) gate times and dynamic ranges on the order of $10^4$ and is disclosed in the technical article of B. B. Das, D. M. Yoo, R. R. Alfano, entitled "Ultrafast Time-Gates Imaging in Thick Tissues: A Step Toward Optical Mammography," published in *Optics Letters*, vol. 18, pp. 1092–1094, Jul. 1993. An additional approach is disclosed in the technical article of D. J. Hall, J. C. Hebden, D. T. Delphy, entitled "Imaging Very-Low-Contrast Objects in Breastlike Scattering Media with a Time-Resolved Method," published in *Applied Optics*, vol. 36, pp. 7270–7276, October 1997. Other related techniques use nonlinear mixing of the received pulse and the delayed transmitted pulse to perform the temporal discrimination, such as that disclosed in the technical article of Bashkansky and J. Reintjes, entitled "Nonlinear-Optical Field CrossCorrelation Techniques for Medical Imaging with Lasers," published in *Applied Optics*, vol. 32, pp. 3842–3845, July 1993, as well as another approach disclosed in the technical article of F. Liu, K. M. Yoo, R. R. Alfano, entitled "Ultrafast Laser-Pulse Transmission and Imaging Through Biological Tissues," published in *Applied Optics*, vol. 32, pp. 554–558, February 1993. The main disadvantage of the time-gated operations included in the time domain approach is that the receiver bandwidth must be large to recover the short transmitted pulse. This increases system complexity and receiver noise.

The coherence domain approach (FIG. 1(B)), transmits a burst of light 38 in the direction 40 into the tissue 16 and uses coherent gate devices, associated with the received section 14, which rely on optical interference between the image-bearing photons (contained in the scattered signal 42). The multiply scattered light consisting of a component 46 associated with the snake light 24 and a component 48 associated with the diffuse light 26 becomes uncorrelated with the transmitted light and does not produce an interference signal. One such coherence approach is more fully described in the technical article of J. A. Izatt, M. D. Kulkarni, K. Kobayashi, M. V. Sivak, J. K. Barton, and A. J. Welsch, entitled "Optical Coherence Tomography for Biodiagnostics," published in *Optics and Photonics News*, vol. 8, pp. 41–47, 1997, whereas another such coherence approach is disclosed by M. R. Hee, J. A. Izatt, J. M. Jacobson, and J. G. Fujimoto, in the technical article entitled "Femtosecond Transillumination Optical Coherence Tomography," published in *Optics Letters*, vol. 18, pp. 950–952, 1993. A further related article is disclosed by A. F. Fercher, entitled "Optical Coherence Tomography," published in *Journal of Biomedical Optics, vol.* 1, no. 2, pp. 157–173, April 1996.

In the coherence domain approach of FIG. 1(B), optical interference occurs only for photons that are coherent with the reference signal. More particularly, optical interference occurs only between signals 38 and 42. Therefore, diffuse, incoherent photons associated with snake light 24 and diffused light 26 are gated out in this approach. Since the length of the gate opening is determined by the coherence length of the reference pulse 38, very short coherence length sources, such as light emitting diodes, are being investigated for use in this technique. Although micrometer resolution of suspected tumors is possible with this technique, the penetration depth to encompass the target 16 is limited to 1–2 mm due to the high degree of optical scattering and subsequent loss of optical coherence.

The frequency domain approach (FIG. 1(C)) is a variation of the time domain method of FIG. 1(A). The frequency domain approach of FIG. 1(C) transmits a signal 50 in the direction 52 into the tissue 16 and uses phase 54 and amplitude 56 measurements associated with the received section 14 to measure the relationship between the ballistic light 22, snake light 24, and diffused light 26, all shown in FIG. 1(C) in the received section 14.

Since the time and frequency domains of the associated transmitted and reflected signals are related through Fourier transforms, approaches similar to the time gating technique can be used in the frequency domain approach. While the time domain approach uses amplitude and time to discriminate multiply scattered, diffuse photons of light from the more direct snake and ballistic photons of light, the frequency domain uses the differences in the amplitude 56 and phase 54 of a modulated optical signal to perform this task.

Since the majority of photons are scattered many times while traversing a very turbid medium, such as that of tissues, previous work has focused on low frequency (<1 GHz) modulation of signal 50 and diffusely scattered light to detect imbedded objects, such as tumors in tissues. One such approach is disclosed in the technical article of M. A. O'Leary, D. A. Boas, B. Chance, A. G. Yodh, entitled "Experimental Images of Heterogeneous Turbid Media by Frequency-Domain Diffusing-Photon Tomography," published in *Optics Letters*, Vol. 20, pp. 426–428, 1995. Further, U.S. Pat. Nos. 6,064,917, 5,917,190, 5,424,843 describe features associated with the frequency domain approach.

The benefits of this frequency domain approach include reduced system complexity and receiver bandwidth. Furthermore, the absorption and scattering properties of the tissue can be calculated through use of diffusion equations and the measured amplitude and phase information. The main disadvantage is that an extremely precise measurement of the phase associated with the transmitted and reflected signals is required to achieve high depth resolution of possible tumors at these low (<1 GHz) modulation frequencies. The other disadvantage is that at these low modulation frequencies, the signal is dominated by diffuse photons that severely degrade the image quality. It is desired to provide a system for detecting the presence of cancerous tumors in tissues that does not suffer the drawbacks of the systems of FIGS. 1(A), 1(B), and 1(C).

OBJECTS OF THE INVENTION

It is an object of the present invention to provide for optical imaging in a tissue to the detection of tissue inhomogeneities, such as a cancerous tumor, by using transmitted light that enters into a volume of target tissue that encompasses suspected tumors and discriminating scattered light associated with the cancerous tumors from the from the diffuse scattered, or backscattered, light associated with normal, healthy tissue.

It is another object of the present invention to provide for relatively high modulation signals that result in improved phase and amplitude sensitivity so as to obtain more accurate detection of cancerous tumors within the tissue.

It is another object of the present invention to provide improved optical imaging by providing a system that combines the advantageous optical penetration features of the lidar system with the advantageous coherent detection schemes of radar.

It is another object of the present invention to provide for relatively high modulation signals that result in improved phase sensitivity so as to obtain more accurate detection of cancerous tumors within the tissue.

SUMMARY OF THE INVENTION

This invention is directed to a hybrid lidar-radar system for detecting the presence of an object which in one form is tissue inhomogeneities, such as cancerous tumors, within the tissue by the detection of reflected and scattered light signals from the tissue and discriminating the information related to the cancerous tumors from the scattering of light created by the tissue itself.

The hybrid lidar-radar system comprises a source of microwave energy, a source of light, an optical detector, and a microwave receiver.

The source of microwave energy provides a microwave subcarrier signal. The source of light provides for, and is transmitted toward the tissue, an optical carrier signal that is modulated by the microwave subcarrier signal. The source of light transports the microwave subcarrier signal through the tissue and is reflected and scattered by the tissue. The detector detects the scattered and reflected light and produces electrical signals indicative thereof.

The optical detector provides an output signal to a network analyzer. The network analyzer receives the produced electrical signals and measures the phase and amplitude differences between the light scattered from the tissue and a reference signal for the detection of the object, that is, in one embodiment the cancerous tumor.

BRIEF DESCRIPTION OF THE DRAWINGS

A better understanding of the present invention may be realized when considered in view of the following detailed description, taken in conjunction with the accompanying drawings wherein:

FIG. 1 is composed of FIGS. 1(A), 1(B), and 1(C), all of which illustrate prior art approaches for the use of light to detect tumorous growth, wherein

DETAILED DESCRIPTION OF THE PREFERRED EMBODIMENTS

Figure 2:
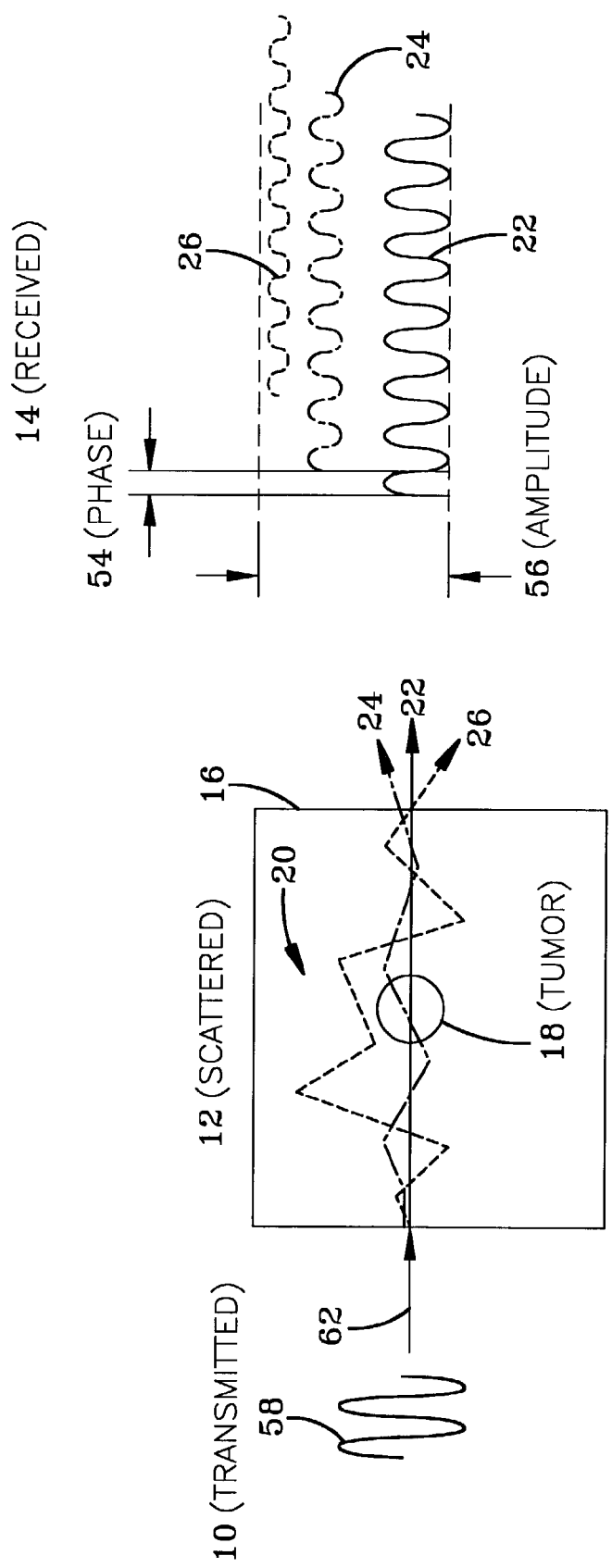
FIG. 2 generally illustrates the practice of the present invention showing the use of modulation frequencies to improve the rejection of multiple scattered, diffused photons from reflected light being examined so as to enhance image contrast and resolution for the detection of cancerous tumors.

With reference to the drawings, wherein the same reference number indicates the same element throughout, there is shown in FIG. 2 an illustration of overall operation of the present invention using modulation frequencies to improve the rejection of multiple scattered, diffused photons from reflected light being examined and to enhance the image contrast and resolution for detecting tumors residing in tissue.

The present invention provides a method for using the system of the present invention for detecting the presence of objects, such as cancerous tumors, within tissues by detecting reflected signals from a tissue and discriminating the information related to the object from the information contained in the backscattered light created by the tissue itself.

The method provides a microwave subcarrier signal, and provides a source of light that is transmitted toward the tissue and is scattered from the tissue and includes an optical signal serving as a reference light signal. The source of light is modulated with the microwave subcarrier signal.

The method detects the modulated reference light signal and the scattered modulated light signals all of which produce electrical signals thereof. The produced electrical signals are measured, preferably by a network analyzer that detects the phase and amplitude difference between the reflected scattered light signal and the modulated reference light signal so as to determine the presence of a cancerous tumor within the tissue being examined. The method of the present invention may be further described with reference to FIG. 2.

Figure 1A:
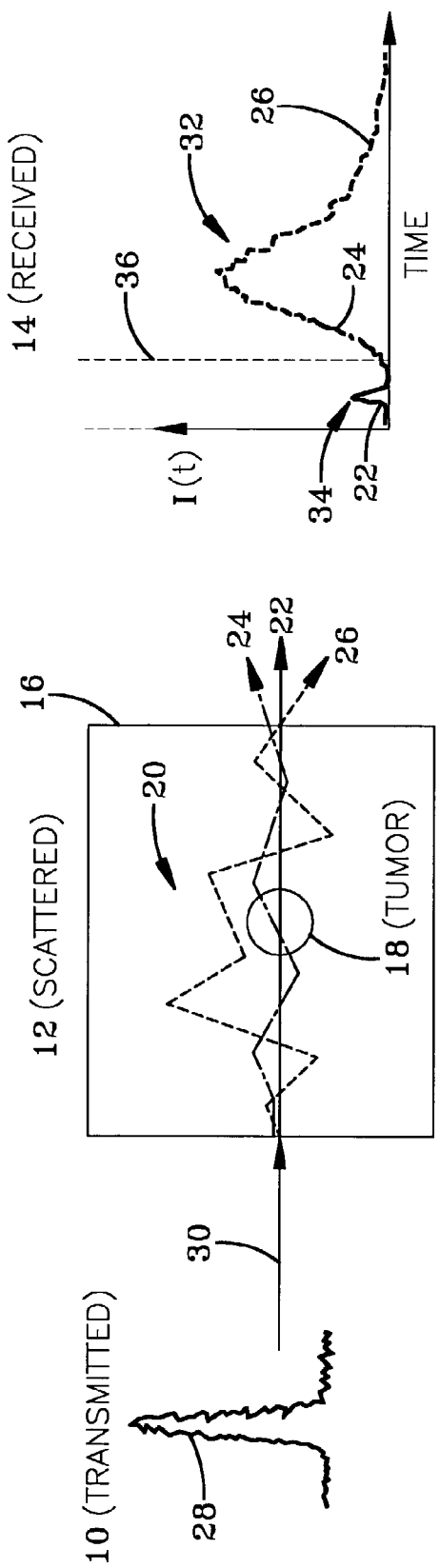
FIG. 1(A) illustrates a prior art time domain approach.
Figure 1B:
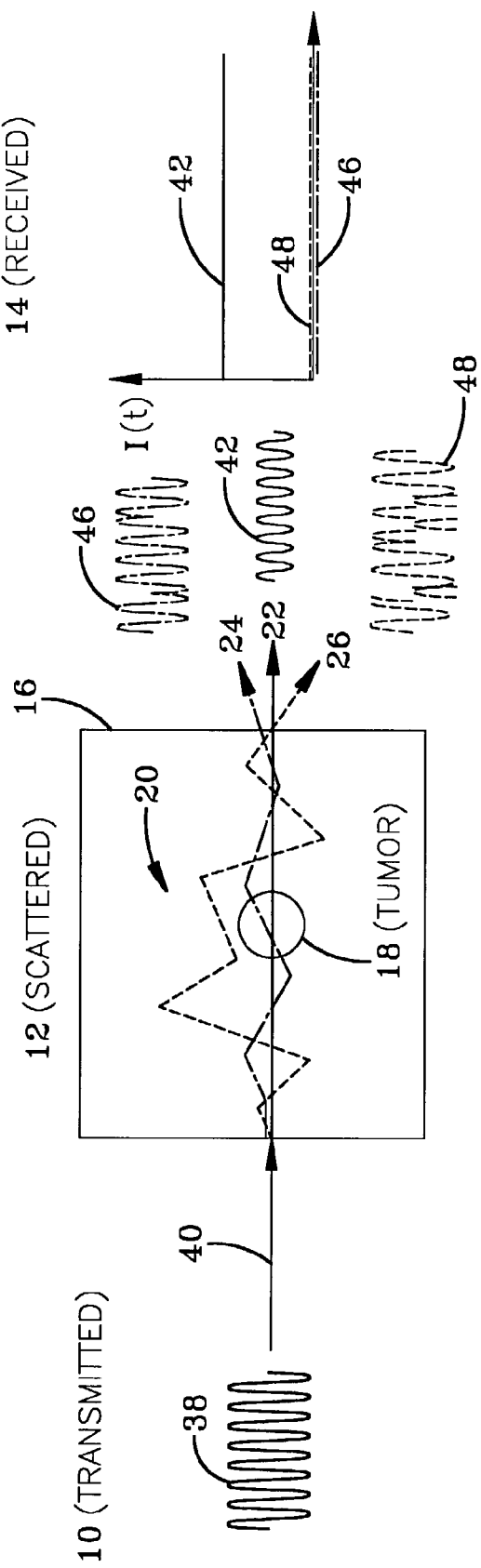
FIG. 1(B) illustrates a prior art coherence domain approach.

FIG. 2 is quite similar to FIG. 1(C) with the exception that FIG. 2 transmits a modulated optical signal 58 with a modulation frequency exceeding 1 GHz, in a manner to be further described with reference to FIG. 3. The modulated optical signal 58 is transmitted in the direction of 62 into the tissue 16 previously described with reference to FIG. 1.

FIG. 2 illustrates the composite signal 20 scattered from the tissue 16, which may include a tumor 18, and is comprised of the ballistic light 22, the snake light 24, and the diffused light 26. FIG. 2 has the received portion 14 similar to that of FIG. 1(C) showing the phase and amplitude measurements 54 and 56, respectively. The system associated with the overall operation illustrated in FIG. 2 is comprised of a hybrid lidar-radar technology.

The basic approach of the hybrid lidar-radar detection scheme of system 64 used in the practice of the present invention is to make use of the way in which each component (22, 24, and 26) of the composite signal 20 is affected by the scattering of the modulated optical signal 58 shown in FIG. 2. Since the diffuse light 26 arises from reflections from a volume of randomly distributed scatterers, the modulation is essentially washed out in this signal component, which is indicated by reference number 26 in the received section of FIG. 2. The snake light 24 that undergoes scattering in small angles and decreases the resolution or sharpness of the image is also de-correlated relative to nonscattered ballistic light 22. Therefore, by tuning the microwave receiver, such as a network analyzer 72, to the modulation frequency, the diffuse 26 and snake 24 signals are reduced relative to the ballistic signals. The success of this approach relies on selecting the proper modulation frequency (or frequencies) to minimize the scattered "noise" signal and maximize the image contrast.

Lidar systems are known and have been developed for a variety of detection purposes, e.g., detection of underwater targets from an airborne platform. The typical lidar system is much like the early radar systems. A short pulse of optical radiation is transmitted, and a receiver measures the reflected return optical power as a function of time. The present invention relates to detection or objects and, more particularly, to techniques in which lidar and radar technologies are combined to improve the resolution and sensitivity for the detection of cancerous tumors within tissues and may be further described with reference to FIG. 3.

Figure 3:
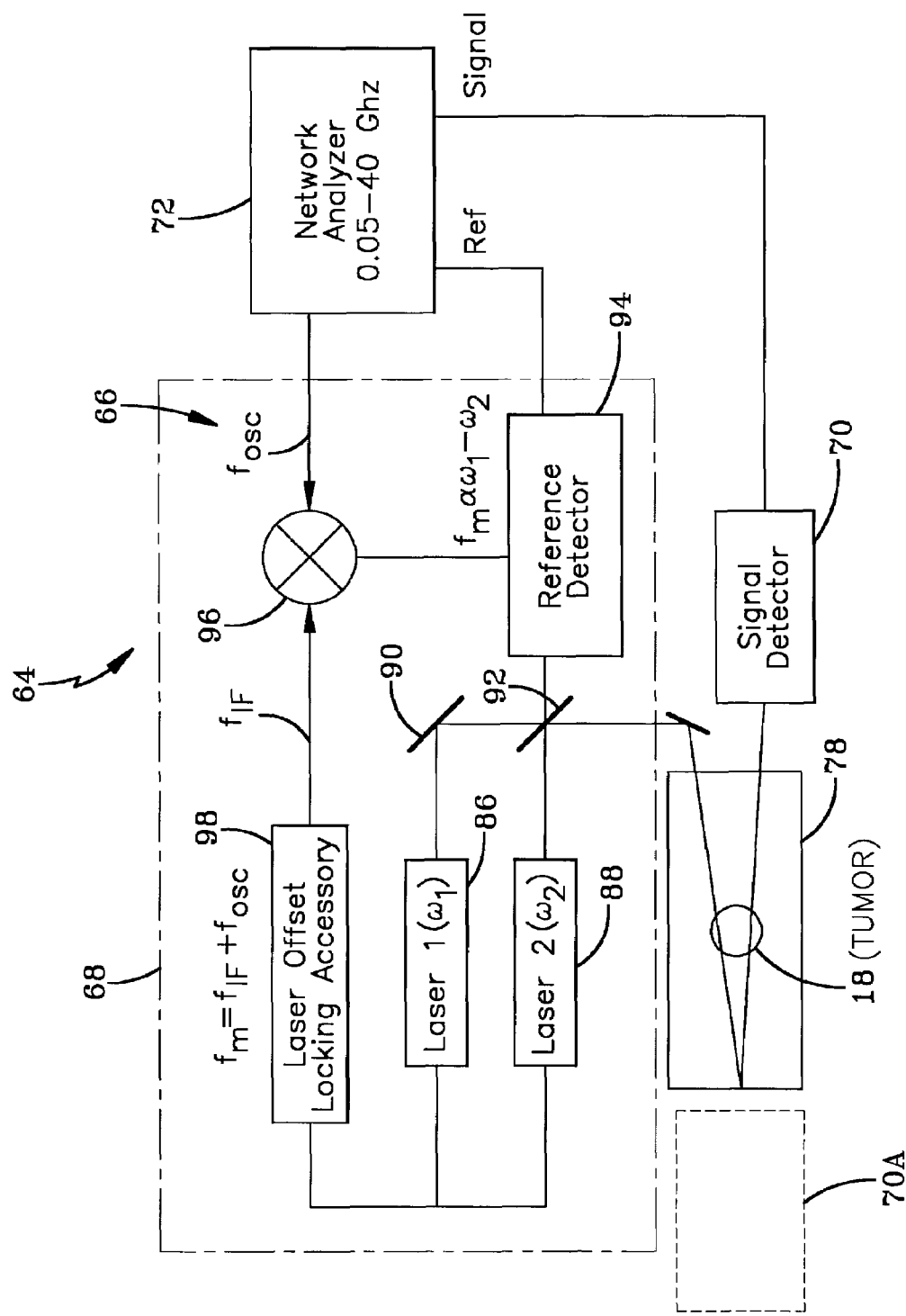
FIG. 3 illustrates a block diagram of the hybrid lidar-radar system of the present invention particularly suited for detecting the presence of cancerous tumors within the tissue.

FIG. 3 illustrates a hybrid lidar-radar system 64 having a source 66 of microwave energy, a source 68 of continuous wave (CW) light that is modulated, a detector 70 for detecting scattered and reflected signals and producing electrical signals, indicative thereof, and a network analyzer 72.

The source of microwave energy 66 provides a reference signal, which is created by the network analyzer 72. The frequency of the microwave energy 66 selects the modulation frequency used in the measurements.

The source of continuous wave light 68 is comprised of first and second lasers 86 and 88, each having an output with the output of the first laser 86 being intercepted by a reflector 90 which, in turn, reflects the output signal thereof to a 50/50 optical splitter 92 which also receives the output of the second laser 88. Each of the first and second lasers has an operating frequency of about 1064nm and provides coherent light having a power level of about 700mW. The lasers 86 and 88 may be temperature tuned so that the optical frequency difference between the two lasers 86 and 88 range from 0.01 to 60GHz.

The source of continuous wave light 68 further comprises a detector 94, a mixer 96, and a laser offset locking assembly 98. The laser offset locking assembly 98 provides an output signal that coerces the output of first and second lasers 86 and 88.

In operation, and with reference to FIG. 3, the technique associated with the present invention for providing the desired modulated optical signal is based on the mixing of two tunable, single frequency Nd:YAG lasers 86 and 88. The lasers 86 and 88 have an optical frequency difference in the range from 0.01–60 GHz. This optical frequency difference generates the desired modulation frequency fm when the two optical signals from lasers 86 and 88 are combined in an optical detector comprises of the 50/50 optical splitter 92 and the detector 94. The desired modulated frequency $f_m$ is shown with reference to detector 94 as $f_{m\ \alpha}\omega_1-\omega_2$. The benefits of the optical heterodyne technique provided by this technique include full 100% modulation depth capability, good linearity, and relatively high optical power.

The hybrid lidar-radar system 64 of FIG. 3 comprises the two (2) 700mW, 1064nm lasers 86 and 88 having an output from the 50/50 optical splitter 92 that is directed to the tissue 78 under test, while the other output of the 50/50 splitter 92 is detected by detector 94 and part of this detected signal is mixed by mixer 96 with a microwave signal 66 to produce the intermediate frequency $f_{IF}$. This intermediate frequency $f_{IF}$ is used by the offset locking accessory 98 to lock the two lasers together to the desired offset frequency which corresponds to the desired modulation frequency $f_M=f_{IF}+f_{osc}$.

Another detector 70 detects the modulated optical signal emanating from the tissue 78 under test. This detected signal (denoted "signal" in FIG. 3) is then fed to the input of the network analyzer 72. The other part of the signal detected by detector 94 (denoted "reference" in FIG. 3) is fed into another input of the network analyzer 72. The network analyzer 72 then measures the amplitude and phase differences between the reference and signal inputs for determination of the presence of a tumor 18. Since the tumor 18 scatters light to a lesser degree than normal, healthy tissue, the light scattered by the tumor 18 will have a smaller phase shift and larger modulation depth (larger amplitude at the network analyzer) than the light scattered by the normal, healthy tissue. Therefore, when the transmitted light beam and detector 70 are scanned over the surface of the tissue 78 under investigation, the presence of a tumor 18 (or other inhomogeneity) is indicated by an increase in amplitude and a reduction in phase relative to the background comprised of normal, healthy tissue.

Figure 1C:
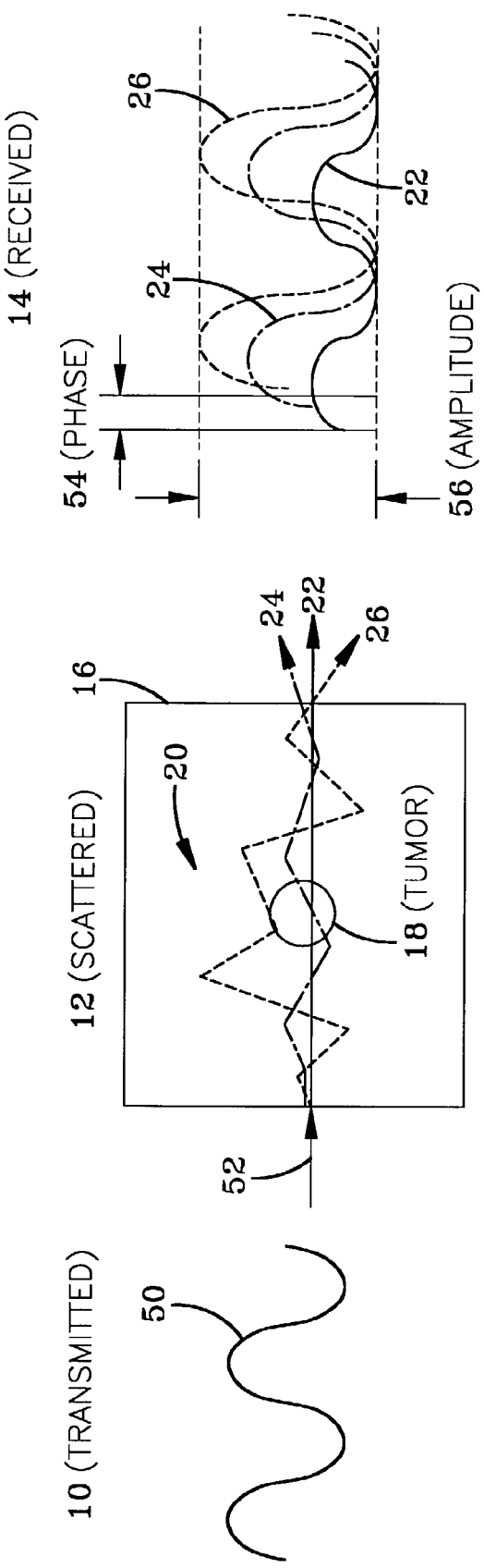
FIG. 1(C) illustrates a prior art frequency domain approach.

It should now be appreciated that the practice of the present invention by providing a higher modulation frequency in the range of 1–40 GHz results in an improved accuracy in detecting tumors in tissue due to the increased phase sensitivity provided by these higher frequencies (as compared to the frequency domain method in FIG. 1(C)). While the present invention has phase sensitivity that is reduced relative to the coherence domain method of FIG. 1(B), the use of a lower frequency subcarrier offers the benefit for deeper penetration into the tissue under examination. This is due to the fact that the approach depicted in FIG. 1(B) relies on maintaining optical coherence for detection, which limits the approach to depths of 1–2 mm. The approach depicted in FIG. 3 relies on maintaining coherence of the modulation signal, which is a factor of 1,000 to 100,000 times larger in wavelength than the optical signal. This results in a higher depth penetration of several centimeters. Further, when compared to the time domain method of FIG. 1(B), the present invention performs similar rejection of multiply scattered light with a much narrower receiver bandwidth. For example, the bandwidth associated with FIG. 1(B) and needed to recover a 1 picosecond pulse is on the order of 1000 GHz, whereas for a continuous wave modulated signal, the receiver bandwidth can be less than 0.001 GHz. This results in reduced noise and improved sensitivity by the practice of the present invention.

Further embodiments of the present invention may be further described with reference to FIG. 3. As shown in FIG. 3, an alternate embodiment of the present invention may be obtained by placing a detector 70A at the opposite end of the tissue sample 78. In addition, single mode transmitters at other optical frequencies, such as 780–850 nm for oximetry measurements (known in the art), may be used with this technique. Furthermore, it is contemplated that the practice of the present invention includes modulation frequencies above 40 GHz.

Obviously, many modifications and variations of the present invention are possible in light of the foregoing teaching. It is, therefore, to be understood that within the scope of the appending claims, the invention may be practiced otherwise than as specifically described.

What we claim is:

1. A hybrid lidar-radar system for detecting the presence of tissue inhomogeneities within tissue by detection of reflected and scattered light signals from the tissue and discriminating information related to cancerous tumors from scattering of light created by the tissue itself, comprising:
    a source of microwave energy for providing a microwave subcarrier signal;
    a source of continuous wave light for providing and for transmitting toward the tissue an optical carrier signal that is modulated by the microwave subcarrier signal, said source of light transports the microwave subcarrier signal through the tissue and is reflected and scattered by the tissue, said optical carrier signal has a frequency and said source of continuous wave light comprises:
        first and second lasers each having an operating wavelength of about 1064 nm, said first and second lasers having an optical frequency difference in a range from 0.01 GHz to 60 GHz, each of said first and second lasers having an output;
        a 50/50 optical splitter receiving and combining the outputs of said first and second lasers, said optical splitter having first and second outputs with the first output of the optical splitter transmitted toward the tissue;
        a light source optical detector for receiving the second output of said optical splitter and a mixer for mixing it with a reference signal having a frequency slightly offset from the desired modulation frequency, said mixer providing an output serving as an offset and having an intermediate frequency; and
        a laser offset locking assembly receiving the output of said mixer and providing an output signal to each of said first and second lasers that provides coherence between said first and second lasers to said offset intermediate frequency;
    a detector for detecting the scattered and reflected light and for producing electrical signals indicative thereof; and
    an optical detector that provides an output signal to a network analyzer that receives said produced electrical signals and measures phase and amplitude differences between the light scattered from the tissue and said optical carrier signal for the detection of said tissue inhomogeneities.

2. The hybrid lidar-radar system according to claim 1, wherein each of said first and second lasers provide coherent light having a power level of about 700 mW.

3. A method using a hybrid lidar-radar system for detecting the presence of tissue inhomogeneities within tissue by detecting reflected and scattered light signals from the tissue and discriminating information related to cancerous tumors from scattering of light created by the tissue itself comprising the steps:

providing a microwave subcarrier signal;
providing a modulator having said microwave subcarrier signal applied thereto;
providing a source of light that provides an optical carrier signal comprising a reference signal that is transmitted toward the tissue;
modulating said optical carrier signal with said microwave subcarrier signal;
detecting said optical carrier signal comprising said reference signal and scattered modulated light signals all of which produce electrical signals thereof; and,
measuring said electrical signals to detect phase and amplitude differences between the reflected and scattered light signal and said reference signal so as to determine the presence of said tissue inhomogeneities.

4. The method according to claim 3, wherein said provided source of continuous wave light comprises first and second lasers each having an operating wavelength of about 1064 nm with the first and second lasers having a 15 optical frequency difference in the range from 0.01 GHz to 60 GHz.

5. The method according to claim 3, wherein said detection is performed by a network analyzer.

* * * * *